United States Patent
Gatenholm et al.

(10) Patent No.: US 11,370,171 B2
(45) Date of Patent: Jun. 28, 2022

(54) CLEAN CHAMBER TECHNOLOGY FOR 3D PRINTERS AND BIOPRINTERS

(71) Applicant: BICO Groug AB, Gothenburg (SE)

(72) Inventors: Erik Gatenholm, Gothenburg (SE); Ivan Tournier, Gothenburg (SE); Paul Gatenholm, Riner, VA (US)

(73) Assignee: Cellink Bioprinting AB, Gothenburg (SE)

( * ) Notice: Subject to any disclaimer, the term of this patent is extended or adjusted under 35 U.S.C. 154(b) by 0 days.

(21) Appl. No.: 15/755,767

(22) PCT Filed: Aug. 31, 2016

(86) PCT No.: PCT/US2016/049716
§ 371 (c)(1),
(2) Date: Feb. 27, 2018

(87) PCT Pub. No.: WO2017/040675
PCT Pub. Date: Mar. 9, 2017

(65) Prior Publication Data
US 2018/0326665 A1 Nov. 15, 2018

Related U.S. Application Data

(60) Provisional application No. 62/212,324, filed on Aug. 31, 2015.

(51) Int. Cl.
*B29C 64/364* (2017.01)
*F24F 13/28* (2006.01)
(Continued)

(52) U.S. Cl.
CPC .............. *B29C 64/364* (2017.08); *B01L 1/02* (2013.01); *B29C 64/245* (2017.08); *B29C 64/25* (2017.08);
(Continued)

(58) Field of Classification Search
CPC .................................................... B29C 64/364
See application file for complete search history.

(56) References Cited

U.S. PATENT DOCUMENTS

| 5,083,558 A | 1/1992 | Thomas et al. | |
|---|---|---|---|
| 5,563,767 A * | 10/1996 | Chen | G11B 33/124 361/679.31 |

(Continued)

FOREIGN PATENT DOCUMENTS

| CN | 204547088 U | 8/2015 |
|---|---|---|
| CN | 205185336 U | 4/2016 |

(Continued)

OTHER PUBLICATIONS

Roger Welker, Continuous Contamination Monitoring Systems, Chapter 4.1.3. Room Pressurization, Elsevier Inc., p. 162 (Year: 2010).*

(Continued)

*Primary Examiner* — Alison L Hindenlang
*Assistant Examiner* — Asha A Thomas
(74) *Attorney, Agent, or Firm* — McCarter & English, LLP (57) ABSTRACT

Clean chamber technology for 3D printers and bioprinters is described. An airtight chamber or enclosure is provided so that positive pressure can be created inside the chamber. Unfiltered air is sucked in from outside into the chamber through a high efficiency filter such as a HEPA filter, using an electrically powered fan or blower, filtering out at least about 99% of particles and contaminants. The filtered air is then pushed into a 3D printing area inside the chamber and out through vents within the frame of the chamber. The technology provides a clean environment for 3D bioprinting of human tissue models and organs and 3D cell culturing without requiring clean room facilities.

12 Claims, 4 Drawing Sheets

(51) Int. Cl.

| | | |
|---|---|---|
| *B01L 1/02* | (2006.01) | |
| *B33Y 40/00* | (2020.01) | |
| *F24F 3/167* | (2021.01) | |
| *B33Y 30/00* | (2015.01) | |
| *B33Y 50/02* | (2015.01) | |
| *B29C 64/264* | (2017.01) | |
| *B29C 64/245* | (2017.01) | |
| *B29C 64/393* | (2017.01) | |
| *B29C 64/25* | (2017.01) | |
| *C12M 3/00* | (2006.01) | |
| *F24F 11/00* | (2018.01) | |
| *B01L 3/02* | (2006.01) | |
| *B33Y 70/00* | (2020.01) | |
| *B33Y 80/00* | (2015.01) | |
| *B29L 31/40* | (2006.01) | |

(52) U.S. Cl.
CPC .......... *B29C 64/264* (2017.08); *B29C 64/393* (2017.08); *B33Y 30/00* (2014.12); *B33Y 40/00* (2014.12); *B33Y 50/02* (2014.12); *C12M 21/08* (2013.01); *F24F 3/167* (2021.01); *F24F 13/28* (2013.01); *B01L 3/0241* (2013.01); *B01L 2200/0636* (2013.01); *B01L 2300/0681* (2013.01); *B29L 2031/40* (2013.01); *B33Y 70/00* (2014.12); *B33Y 80/00* (2014.12); *F24F 2011/0004* (2013.01)

(56) References Cited

U.S. PATENT DOCUMENTS

| | | | |
|---|---|---|---|
| 6,722,872 B1 | 4/2004 | Swanson et al. | |
| 6,905,645 B2 * | 6/2005 | Iskra ...................... | B33Y 10/00 264/128 |
| 7,051,654 B2 | 5/2006 | Boland et al. | |
| 7,939,003 B2 | 5/2011 | Bonassar et al. | |
| 8,143,055 B2 | 3/2012 | Forgacs et al. | |
| 8,915,984 B2 | 12/2014 | Kawasaki et al. | |
| 9,499,779 B2 | 11/2016 | Murphy et al. | |
| 9,752,116 B2 | 9/2017 | Forgacs et al. | |
| 9,855,369 B2 | 1/2018 | Murphy et al. | |
| 2015/0321419 A1 * | 11/2015 | Linthicum ............. | B33Y 30/00 264/308 |
| 2015/0375453 A1 * | 12/2015 | Yost ....................... | C12N 11/04 435/174 |
| 2016/0236407 A1 * | 8/2016 | Armani ................. | B29C 64/118 |

FOREIGN PATENT DOCUMENTS

| | | |
|---|---|---|
| CN | 105642891 A | 6/2016 |
| CN | 104758085 B | 11/2016 |
| EP | 2914433 A1 | 5/2014 |
| JP | 2009047613 A | 3/2009 |
| JP | 4701458 B2 | 3/2011 |
| RU | 28639 U1 | 4/2003 |
| SU | 1112193 A | 9/1984 |
| WO | WO 92/07542 A | 5/1992 |
| WO | WO 2015/017579 A1 | 2/2015 |
| WO | WO 2016/044837 A1 | 3/2016 |

OTHER PUBLICATIONS

"Qingdao Unique to 3D print skin and corneas within one year", Blog, Quidao L.P.D. Co., Ltd. Mar. 25, 2015; http://www.3ders.org/articles/20150325-qingdao-unique-to-3d-print-skin-and-corneas-within-one-year.html, accessed Feb. 26, 2018.

International Search Report and Written Opinion, prepared by the Federal Institute of Industrial Property in Moscow, Russia, acting as the International Searching Authority, for nternational application PCT/US2016/049716 dated Jan. 12, 2017.

Third Party Observations filed for International Application PCT/US2016/049716, date of submission is Dec. 11, 2017.

Office action issued by the Korean Patent Office for counterpart Korean application, 10-2018-7011462, dated May 1, 2018 in Korean with English translation.

Dennis, Sarah Grave et al.: "Deposition of Cell-Laden Hydrogels in a Complex Geometry Using a 3D BioPrinter", *Microscopy and Microanalysis*, 21 (Supplement 3), 2015, pp. 621-622 (including $3^{rd}$ party observations summary as cover page, previously submitted).

Dennis, Sarah Grace: "Microscopy and Microanalysis 2015 Conference Schedule", from Conference in Portland, Oregon entitled *Microscopy and Microanalysis 2015*, Conference date Aug. 2, 2015, pp. 78-79 (including $3^{rd}$ party observations summary as cover page, previously submitted).

musc.edu: "Insight into possible future of growing organs for transplant", obtained from http://academicdepartments.music.edu/newscenter/2015/biofabrication-lab-tour-michael-yost.html#.Wi3veiPMyay, accessed Dec. 10, 2017 (including $3^{rd}$ party observations summary as cover page, previously submitted).

Golson, Katie: "The Palmetto Printer: 3-head bioprimer developed for MUSC", http://www.katiegolson.com/blog/the-palmetto-printer-3-head-bioprinter-developed-for-musc, accessed Dec. 5, 2017 (including $3^{rd}$ party observations summary as cover page, previously submitted).

Reuters.com: "Biofabrication brings lab-grown tissue closer to reality", http://www.reuters.com/video/2014/09/08/biofabrication-brings-lab-grown-tissue-c?videoId=341724857&videoChannel=2602, accessed Dec. 5, 2017 (including $3^{rd}$ party observations summary as cover page, previously submitted).

Golson, Katie: "3D bioprinter", http://www.youtube.com/watch?v=HDO9qmkWS8o, accessed Dec. 5, 2017 (including $3^{rd}$ party observations summary as cover page, previously submitted).

Scharr, Jill: "Afinia H800 3D Printer Stops Odor with HEPA Air Filters", *Tom's Guide*, http://www.tomsguide.com/us/afinia-h800-3d-printer.news-20218.html, accessed Dec. 5, 2017(including $3^{rd}$ party observations summary as cover page, previously submitted).

3DEngr.com: "WiiBoox One Mini Review", Aug. 22, 2015, retrieved from http://www.3dengr.com/wiiboox-one-mini-review.html, accessed Mar. 11, 2019.

AFINIA 3D: "Afinia H800 3D Printer User's Manual—Version 1.2", Aug. 30, 2015, retrieved from http://web.archive.org/web/20160222000359if_/http://www.afinia.com:80/afinia-downloads/AfiniaH800-3D-Printer-UsersManual.pdf, accessed Mar. 8, 2019.

Goehrke, Sarah Anderson: "3DPrintClean Enclosure Offers 2-Step Filtration to Clean up 3D Printing Process, Enhance Performance", Feb. 23, 2015, retrieved from https://3dprint.com/46250/3dprintclean-filter-enclosure/, accessed Mar. 8, 2019.

Sher, Davide: "The Top 15 Bioprinters", Aug. 26, 2015 retrieved from https://3dprintingindustry.com/news/top-10-bioprinters-55699/, accessed Mar. 11, 2019.

Supplementary Partial European Search Report prepared by European Patent Office for corresponding European application 16842913.2, dated Mar. 26, 2019.

Sher, Davide: "The Top 15 Bioprinters", Sep. 1, 2015 retrieved from https://3dprintingindustry.com/news/top-10-bioprinters-55699/, accessed Sep. 25, 2019 with attached Statement from author, Davide Sher, and emails correcting priority date of reference.

RepRap: "Air ventilation in heated chamber?", posted Sep. 19, 2015. See https://reprap.org/forum/read.php?1.560392, accessed. Aug. 28, 2020.

RepRap: "Open or closed 3D printer?", posted Dec. 27, 2015. See https://reprap.org/forum/read.php?1.601368, accessed Aug. 28, 2020.

Inventia Rastrum 3D Bioprinter designed by Inventia Life Science Design & Industry, Good Design Australia 2019. See https://good-design.org/projects/inventia-rastrum-3d-bioprionter/, accessed Aug. 31, 2020.

Krassenstein, Brian: "Swedish Designed ZYYX 3D Printer Unveiled with Built-in Air Filtration", Jul. 18, 2014, 3D Print.Com the Voice of 3D Printing. See https://3dprint.com/9538/zVyx-3d-printer/ accessed Aug. 28, 2020.

"Rokit Releases a New 3D Bioprinter, Expected to 'Change the Landscape' of Bioprinting" See http://iographix.com/biog/rokit-releases-a-new-3d-bioprinter-expected-to-change-the-landscape-of- (56) References Cited

OTHER PUBLICATIONS bioprinting, accessed Aug. 28, 2020. See also https://3dprint.com/120354/rokit-3d-bioprinter-invivo/, accessed. Aug. 31, 2020.
Foehnstrum: "The crossflow fan approach" Third party products & modifications, Dec. 30, 2013, Ultimaker Community of 3D Printing Experts. See http://community.ultimaker.com/topic/3586-the-crossflow-fan-approach/, accessed Aug. 28, 2020.
"BioBots-3D: Print Your Own Organs" dated May 6, 2015. See https://youtube.com/watch?v=xp2kiPYigqEi&t=284s, accessed Sep. 23, 2020.
Lim, Dr. Mayasari: "Se3 d workshop presentation biolink" published on Jun. 18, 2016. See https://slideshare.net/bio-link/se3-d-workshop-presentation-biolink, accessed Aug. 31, 2020.
"3D printer reprap with dual Bowden and heated chamber", dated Oct. 18, 2014. See https://youtube.com/watch?v=ZHIBtuTJiw8, accessed Sep. 23, 2020.
Bhattacharjee, Nirveek et al.: "The upcoming 3D-printing revolution in microfluidics", *Lab Chip*, 2016, 16, pp. 1720-1742.
Sentry Air Systems: "Portable Clean Room Hood—12" Wide Model #SS-212-PCR ISO Class 5", dated Dec. 20, 2013, p. 1-1.
Dennis, Sarah Grace et al.: "Deposition of Cell-Laden Hydrogels in a Complex Geometry Using a 3D BioPrinter", *Microscopy and Microanalysis*, vol. 21, No. Supp 3, dated Aug. 4, 2015, pp. 621-622.
Apogee Science: "BuzzBox—3D Printer Enclosure by Apogee Science—Kickstarter", dated Feb. 23, 2015, pp. 1-30.
Anonymous: "This New Lab: DIY Cleanroom",*ihrchive Robotics and Engineering Blog Archive*, dated Feb. 28, 2010, pp. 1-21.
Extended European Search Report for corresponding European application 21166018.8 (division of European application 16842913.2) dated Jun. 7, 2021.

\* cited by examiner

CLEAN CHAMBER TECHNOLOGY FOR 3D PRINTERS AND BIOPRINTERS

CROSS-REFERENCE TO RELATED APPLICATIONS

This application is the National Stage entry under 35 U.S.C. § 371 of International Application Number PCT/US2016/049716 filed on Aug. 31, 2016, published on Mar. 9, 2017 under publication number WO 2017/040675 the disclosure of and claims priority to and the benefit of the filing date of U.S. Provisional Application No. 62/212,324, filed Aug. 31, 2015, the disclosures of which are hereby incorporated by reference herein in their entirety.

BACKGROUND OF THE INVENTION

Field of the Invention

The present invention relates to 3D printers and bioprinters, and more particularly, to technology that provides a clean-air operating environment, with reduced contaminants, pollutants and particles, for 3D printers and bioprinters without the use of clean room facilities.

Description of Related Art

Three-dimensional (3D) printing and 3D bioprinting are additive manufacturing technologies in which a material or biomaterial can be deposited layer by layer in a predetermined pattern using a 3D printer or bioprinter. In 3D bioprinting, the biomaterial may be any form, such as liquid, hydrogel or paste-like, and it can be mixed with animal or human cells to produce tissue models or organs. Sterility is a major issue in these operations. It is normally solved by placing the 3D bioprinter in a clean room, which is very expensive and limited to special certified facilities. Thus, there is a need in the art for improvements which overcome these disadvantages.

SUMMARY OF THE INVENTION

Embodiments of the invention provide clean chamber technology for 3D printers and bioprinters. In embodiments, the technology provides a clean environment for 3D bioprinting of human tissue models and organs and 3D cell culturing without requiring clean room facilities. In one embodiment, a chamber or enclosure with a metallic frame is provided which is fully or relatively airtight so that positive pressure can be created inside the printing chamber. Unfiltered air is drawn from outside into the chamber through a high efficiency filter such as a High-Efficiency Particulate Arresting (HEPA) filter, using an electrically powered fan, filtering out at least about 99% of particles and contaminants. The filtered air is then blown preferably in a very smooth, laminar flow towards into the printing chamber and out through vents within the frame.

Embodiments of the invention provide a clean chamber which includes a housing and an air supply unit and one or more vents disposed within the housing. The housing is adapted to house a 3D printer or bioprinter and has a volume that is less than 1 $m^3$. The air supply unit and one or more vents can be configured to provide laminar air flow inside the housing. The laminar flow may be vertical or horizontal. The air supply unit includes a high efficiency filter and a fan and the high efficiency filter can be a HEPA filter or an Ultra Low Penetration Air (ULPA) filter. The air supply unit and one or more vents are configured to provide positive pressure inside the housing, such as a positive pressure differential of 0.02 in. to 0.2 in water column. The housing further includes doors or ports configured to provide access to the 3D printer or bioprinter as well as windows adapted for viewing the 3D printer or bioprinter. The housing further includes a sealing system around the windows and doors to make the housing airtight. The housing can be constructed of materials which include one or more of steel, stainless steel, aluminum, titanium, glass, or plastic, or any combination thereof.

Additional embodiments of the invention provide a laboratory instrument which includes a clean chamber, which clean chamber includes a housing and an air supply unit and one or more vents disposed within the housing. The laboratory instrument further includes a 3D printer which includes a 3D printing platform or print bed and one or more fluid sources adapted for 3D printing disposed above the print bed. The 3D printer is disposed within the housing such that the 3D print bed is disposed between the air supply unit and the one or more vents. Further, the clean chamber is capable of maintaining positive pressure inside by way of the air supply unit such as a positive differential pressure in the range of 0.02 in. to 0.2 in water column. In embodiments, the housing further includes one or more controls or displays for interfacing with the 3D printer. The housing further includes a door adapted for providing access inside the housing and at least one window adapted for viewing inside the housing. The air supply unit is disposed at the top of the housing and the one or more vents are disposed at the sides or the bottom of the housing. In this embodiment, the air supply unit and one or more vents are configured to provide vertical laminar air flow which is disposed above the 3D print bed. In embodiments, the air supply unit comprises a fan and a high efficiency filter such as a HEPA filter or an ULPA filter. The housing is made of a material which includes one or more of steel, stainless steel, aluminum, titanium, glass, or plastic. In embodiments, the instrument is dimensioned to be less than 0.5 $m^3$ (such as less than 3 $m^3$, less than 2 $m^3$, less than 1 $m^3$) and/or preferably has a footprint (such as a base with a length and width) that is smaller than the depth of a standard laboratory bench, i.e. 60 cm.

Specific aspects of the invention include Aspect 1, a clean chamber comprising: a housing; an air supply unit and one or more vents disposed within the housing; wherein the housing is adapted to house a 3D printer or bioprinter; wherein the housing has a volume that is less than 1 $m^3$.

According to Aspect 2, the clean chamber of Aspect 1 can be configured such that the air supply unit and/or one or more vents are configured to provide laminar air flow inside the housing.

Aspect 3 provides for a clean chamber of Aspect 1 or 2 configured to provide for a vertical laminar air flow.

Aspect 4 is a clean chamber of any of Aspects 1-3 configured to provide for a horizontal laminar air flow.

Aspect 5 is a chamber of any of Aspects 1-4, wherein the air supply unit comprises a filter and/or a fan.

Aspect 6 provides for a clean chamber of any of Aspects 1-5, wherein the filter is a HEPA filter or an ULPA filter.

Aspect 7 is a clean chamber of any of Aspects 1-6, wherein the air supply unit and/or one or more vents are configured to provide a positive pressure differential inside the housing.

Aspect 8 is a clean chamber of any of Aspects 1-7, wherein there is a positive pressure differential inside the housing which is in the range of 0.02 in. to 0.2 in water column.

Aspect 9 is a clean chamber of any of Aspects 1-8, wherein the housing further comprises doors or ports configured to provide access to the 3D printer or bioprinter.

Aspect 10 is a clean chamber of any of Aspects 1-9, wherein the housing further comprises windows adapted for viewing the 3D printer.

Aspect 11 is a clean chamber of any of Aspects 1-10, further comprising a sealing system around windows and/or doors of the housing.

Aspect 12 is a clean chamber of any of Aspects 1-11, wherein the housing comprises one or more of steel, stainless steel, aluminum, titanium, glass, or plastic.

Aspect 13 is a clean chamber comprising: a housing adapted to house a 3D printer or bioprinter; an air supply unit and one or more vents disposed within the housing; a plurality of windows and doors disposed within the housing that provide viewing or access to portions of the 3D printer or bioprinter; a sealing system around the doors and windows of the housing; wherein the housing has a volume that is less than 1 $m^3$; wherein together the air supply unit, one or more vents, and sealing system are configured to provide positive pressure inside the housing.

Aspect 14 is the clean chamber of Aspect 13, wherein the housing is integrated with the 3D printer or bioprinter.

Aspect 15 is a clean chamber of Aspect 13 or 14, wherein the positive pressure inside the housing is in the range of 0.02 in. to 0.2 in water column.

Aspect 16 is a clean chamber of any of Aspects 13-15, wherein the air supply unit and/or one or more vents are configured to provide vertical laminar flow.

Aspect 17 is a clean chamber of any of Aspects 13-16, wherein the air supply unit and/or one or more vents are configured to provide horizontal laminar flow.

Aspect 18 is a clean chamber of any of Aspects 13-17, wherein the air supply unit comprises a filter and/or a fan.

Aspect 19 is a clean chamber of any of Aspects 13-19, wherein the clean chamber comprises a filter and the filter is a HEPA filter or an ULPA filter.

Aspect 20 is a clean chamber of any of Aspects 13-20, wherein the housing comprises one or more of steel, stainless steel, aluminum, titanium, glass, or plastic.

Aspect 21 is a laboratory instrument, comprising: a clean chamber, comprising: a housing; an air supply unit and one or more vents disposed within the housing; and a 3D printer comprising: a 3D print bed; one or more fluid sources adapted for 3D printing disposed above the print bed; wherein the 3D printer is disposed within the housing such that the 3D print bed is disposed between the air supply unit and the one or more vents; wherein the clean chamber is capable of maintaining positive pressure inside by way of the air supply unit.

Aspect 22 is a laboratory instrument of Aspect 21, wherein the housing further comprises one or more controls and/or displays for interfacing with the 3D printer.

Aspect 23 is a laboratory instrument of Aspect 21 or 22, wherein the housing further comprises a door adapted for providing access inside the housing.

Aspect 24 is a laboratory instrument of any of Aspects 21-23, wherein the housing further comprises at least one window adapted for viewing inside the housing.

Aspect 25 is a laboratory instrument of any of Aspects 21-24, wherein the air supply unit is disposed at the top of the housing and/or the one or more vents are disposed at the sides or the bottom of the housing.

Aspect 26 is a laboratory instrument of any of Aspects 21-25, wherein the air supply unit comprises a fan and/or a filter.

Aspect 27 is a laboratory instrument of any of Aspects 21-26, wherein the laboratory instrument comprises a filter and the filter is a HEPA or an ULPA filter.

Aspect 28 is a laboratory instrument of any of Aspects 21-27, wherein the housing comprises one or more of steel, stainless steel, aluminum, titanium, glass, or plastic.

Aspect 29 is a laboratory instrument of any of Aspects 21-28, wherein the positive pressure is a positive differential pressure in the range of 0.02 in. to 0.2 in water column.

Aspect 30 is a laboratory instrument of any of Aspects 21-29, wherein the air supply unit and/or one or more vents are configured to provide vertical laminar flow.

Aspect 31 is a laboratory instrument of any of Aspects 21-30 configured to provide for a vertical laminar flow disposed above the 3D print bed.

Aspect 32 is a laboratory instrument of any of Aspects 21-31, wherein the instrument is dimensioned to be less than 3 $m^3$, less than 2 $m^3$, less than 1 $m^3$, or less than 0.5 $m^3$.

Aspect 33 is a laboratory instrument of any of Aspects 21-32, wherein the instrument is dimensioned to be less than 0.5 $m^3$.

Aspect 34 is a laboratory instrument of any of Aspects 21-33, wherein the instrument is dimensioned to have a footprint that is smaller than the width of a standard laboratory bench.

Aspect 35 is a laboratory instrument of any of Aspects 21-34, wherein the 3D printer is a 3D bioprinter.

Aspect 36 is a laboratory instrument of any of Aspects 21-35, wherein the 3D print bed or platform is adapted to support a multiwell plate or a petri dish.

Aspect 37 is a clean chamber or a laboratory instrument of any of Aspects 1-36, further comprising a UV light source.

BRIEF DESCRIPTION OF THE DRAWINGS

The accompanying drawings illustrate certain aspects of embodiments of the present invention, and should not be used to limit the invention. Together with the written description the drawings serve to explain certain principles of the invention.

DETAILED DESCRIPTION OF VARIOUS EMBODIMENTS OF THE INVENTION

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

In one embodiment, the present invention provides a clean chamber adapted to house or contain a 3D printer such as a 3D bioprinter. The clean chamber may be a separate housing that surrounds the 3D printer, or may be integrated with the 3D printer. The clean chamber is sized such that it is adapted to surround or encompass the 3D printer while minimizing additional space. The inventive clean chamber provides a zone of purified air surrounding the 3D printer that can be housed in a standard laboratory facility that does not meet clean room specifications.

Thus, in some embodiments, the clean chamber is a small sized unit, smaller than 1 $m^3$, with an integrated air supply unit. Dimensions of the clean chamber may vary, but are typically configured such that the clean chamber takes up a volume that is less than 10×, 9×, 8×, 7×, 6×, 5×, 4×, 3×, or 2× the volume of the 3D printer itself. In some embodiments, the volume of the clean chamber is less than 1.9×, 1.8×, 1.7×, 1.6×, 1.5×, 1.4×, 1.3×, 1.2×, 1.1× the volume of the 3D printer. The shape of the clean chamber can vary, but generally a square or rectangular cuboid, or box-like shape, is preferred. Exemplary dimensions of the clean chamber include 100 cm×90 cm×90 cm, 90 cm×80 cm×80 cm, 80 cm×80 cm×80 cm, 90 cm×90 cm×80 cm, 95 cm×80 cm×80 cm, 80 cm×80 cm×75 cm, 75 cm×75 cm×75 cm, 80 cm×70 cm×70 cm, 70 cm×70 cm×70 cm, 60 cm×60 cm×60 cm, 50 cm×50 cm×50 cm, and so on. In embodiments, the dimensions of the clean chamber can accommodate any 3D printer or bioprinter, including inkjet, laser-assisted, and extrusion 3D printers or bioprinters. In certain embodiments, the clean chamber is dimensioned to have a footprint that fits on a standard laboratory bench and is less than 0.5 $m^3$ in volume, such as 40 cm×40 cm×50 cm, and 40 cm×40 cm×40 cm and has a weight in the range of 30-50 lbs, which includes the 3D bioprinter inside. In specific embodiments, the clean chamber has exemplary dimensions of 33 cm×30 cm×38 cm or 33 cm×30 cm×47 cm and has a weight of approximately 40 lbs, including the 3D bioprinter.

In embodiments, the clean chamber provides transparent windows and doors for viewing or access to various components of the 3D printer. For example, the windows and door may provide viewing or access to components such as motors, print heads, print bed, substrates for printing, printed structures, cartridges, syringes, platforms, lasers and controls. Additionally, the clean chamber may provide ports for cables which connect to the 3D printer, such as power cables, USB cables, and the like.

In one embodiment, the clean chamber provides transparent windows for viewing specific operating components of the 3D printer. The transparent windows may be made of glass, plexiglass, plastic, or the like. Some embodiments provide arm ports with sleeves and gloves made of an airtight material such as acrylic, PVC, rubber, or polypropylene. In this embodiment, the clean chamber allows the operator access to the 3D printer while maintaining a clean air environment inside the clean chamber surrounding the 3D printer. Alternatively or in addition, doors or ports can be provided which allow the operator to insert or remove materials inside the chamber and allow access to the 3D printer. The doors or ports can be designed to minimize the introduction of particulate matter inside the chamber. In some embodiments, the doors and ports are transparent to provide for viewing of the 3D printer and can be made of glass, plexiglass, or plastic. The doors or ports may have an airtight sealed closed position, or an open position which allows access to the 3D printer. In the open position, the positive pressure environment inside the clean chamber ensures that no contaminants are introduced inside the chamber. Alternatively or in addition, the clean chamber can be equipped with an Ultraviolet C germicidal lamp (100-280 nm, 4.43-12.4 eV) to sterilize the interior of the 3D printer, particularly the print bed, before usage to prevent contamination by inactivating bacteria, viruses, and protozoa that may enter the clean chamber. The doors or ports are optimally positioned to allow access to various components of the 3D printer or bioprinter that may need removal or replacement, such as syringes containing printing materials, or 3D printed materials from the print bed of the printer. The doors or ports may also provide access to operating controls of the printer. Additionally, the clean chamber can be integrated with the 3D printer or bioprinter in a manner which allows for operation of the 3D printer while maintaining a clean air environment. For example, the print bed of the 3D printer may be configured as or enclosed in a sliding access door or tray that allows removal of 3D printed products. Again, the positive pressure environment maintained by the air supply unit ensures that unfiltered air does not enter the clean chamber when sliding access door or other ports are open. In another embodiment, the controls of the 3D printer are provided outside the housing of the clean chamber, and transmit commands to the 3D printer. In this way, the 3D printer is controlled without an operator having to breach the airtight housing to control the printer. Alternatively, the housing may have USB ports which are wired to the 3D printer, and the 3D printer can be controlled through a computer, motherboard or processor connected to the housing through the USB ports. The firmware installed in the computer of the 3D printer can be programmed to control the speed of the fan or blower in the high efficiency filtration system through a micro controller and a metal-oxide-semiconductor field-effect transistor or any other type of transistor used for amplifying or switching electronic signals. Alternatively, the speed of the fan or blower can be controlled through the software interface in an external computer device. The air flow speed, high efficiency filter life cycle and particle count in the clean chamber can be displayed in the touch-screen or LCD display in the 3D printer and in the software interface.

In embodiments, a sealing system is provided around the windows, doors, and/or ports of the clean chamber. The sealing system can be made of rubber, silicone, or foam in combination with an adhesive. The sealing system ensures that the clean chamber may maintain a positive pressure environment when air is introduced inside the chamber. The sealing system can be disposed at the interface of the windows and doors with the housing to ensure the inside of the housing is airtight or substantially airtight. Such airtight housing allows the air supply unit (described below) to maintain a positive pressure inside the housing.

In embodiments, the clean chamber includes an air supply unit. The air supply unit includes a blower or fan in communication with a high efficiency filter. The high efficiency filter may be a High-Efficiency Particulate Arresting (HEPA) filter, Ultra Low Penetration Air (ULPA) filter, or the like. In particular embodiments, the high efficiency filter may be, at a minimum, a HEPA filter class EU10, which has an efficiency of 95-99.9%. In other embodiments, the HEPA filter may be up to class U17, which has an efficiency of 99.999995%. Embodiments provide a filtration system which brings non-filtered air from the outside environment of the bioprinter and pushes it through the high efficiency filter with the help of a fan to the inside of the clean chamber, when moving volumes of air with small increase in pressure, or with the help of a blower, when moving volumes of air with moderate increase of pressure. Alternatively, the air can be pushed through the high efficiency filter using an air pump. The filtration system is designed so that all of the air drawn into bioprinter is expelled through the filter such that none of the air leaks past the filter. In embodiments, the filtration system is capable of covering an area between 25 cm² and 2 m², such as an area of about 25 cm², 50 cm², 75 cm², 1 m², 1.25 m², 1.5 m², 1.75 m², or 2 m² or higher depending on the size of the printer or bioprinter and number of print heads that the clean chamber must accommodate. In embodiments, the volume of air that can be treated can range up to 1 m³, up to 2 m³, up to 3 m³, up to 4 m³, up to 5 m³, or up to 6 m³ and so on depending on the bioprinter requirements. Additionally, the filtration system can incorporate high-energy UV light units to kill off the live bacteria and viruses trapped by the high efficiency filter.

In some embodiments, the high efficiency filter is placed ahead of the output of the blower or fan such that the filter directly receives the output. In other embodiments, the high efficiency filter is placed behind the blower or fan such that incoming air first passes through the filter before entering the blower or fan. In other embodiments, two high efficiency filters are placed, with one placed before the blower or fan and one placed after the blower or fan. The blower or fan may have a single phase electric motor, or alternatively, a three phase motor. Further, the electric motor may run on AC or DC electric power sources. Alternatively or in addition, the blower or fan may be powered by a battery such that the clean chamber is operable during power outages. Further, in embodiments the blower or fan is configured to have different speeds. One particular embodiment provides a variable speed fan that is driven by a variable speed drive. The variable speed fan provides for precise control of air flow inside the clean chamber. The air supply unit is operated at a flow which is designed to maintain a positive pressure differential inside the chamber in comparison to the outside pressure. Thus, should any leaks in the sealing system occur, the pressurized air inside the chamber will leak outward rather than inward, ensuring that contaminated air does not leak in.

In some embodiments, the high efficiency air filter(s) filter out at least 99% of the particles from ambient air surrounding the chamber. In other embodiments, the high efficiency air filter(s) filters out at least about 95%, 96%, 97%, 98%, 99%, 99.1%, 99.2%, 99.3%, 99.4%, 99.5%, 99.6%, 99.7%, 99.8%, 99.9%, 99.95%, 99.96%, 99.97%, 99.98%, 99.99%, 99.995%, 99.999%, 99.9999%, 99.99999%, 99.999995% or more of particles of 0.30 microns or greater from ambient air surrounding the chamber. In embodiments, the high efficiency air filter(s) provide a sterile, or almost sterile environment inside the chamber. This allows for 3D manufacturing of printed tissues or organs.

In some embodiments, the air supply unit is positioned on top of the clean chamber and receives unfiltered air from the surrounding laboratory environment. The air supply unit then pushes filtered air downwards so that it surrounds the 3D printer while creating and maintaining a positive pressure environment inside the chamber. After passing the 3D printer, the filtered air exits the clean chamber through one or more vents positioned on the bottom of the clean chamber. In this way, the clean chamber provides a laminar or unidirectional (i.e. vertical) stream of filtered air across the 3D printer. However, in some embodiments, the clean chamber is configured to provide a horizontal laminar flow by changing the position of the air supply unit and/or vents.

In other embodiments, the clean chamber is configured to have non-unidirectional (e.g. turbulent) or mixed air flow patterns.

In embodiments, the air supply unit creates a positive pressure inside the chamber that is higher than the ambient pressure surrounding the chamber by having an air flow that is higher than the output through the exhaust vents. This can be achieved by constricting flow through the exhaust vents through obstruction or coupling the exhaust vents with a fan to provide an exhaust unit that has an output that is lower than the fan of the air supply unit. In this way, the exhaust vents ventilate the air and assist in controlling the air flow and pressure inside the clean chamber. The positive pressure inside the chamber is preferably higher than 1 atmosphere pressure (atm). In some embodiments, the differential pressure inside the chamber is in the range of 0.02 in. to 0.2 in water column ($H_2O$), which is similar to the positive pressure inside standard clean rooms. However, in some embodiments, the outputs of the air supply units and exhaust units can be adjusted to provide negative pressure inside the chamber. In some embodiments, multiple air supply units and/or exhaust units are used to move air through the clean chamber. In some embodiments, the clean chamber is equipped with pressure sensors for measuring the air pressure inside the chamber and displays on the outer portion of the housing for displaying the air pressure.

In some embodiments, the air supply unit provides a flow inside the clean chamber at a rate of at least 1 foot/minute. In some embodiments, the air supply unit provides a flow inside the clean chamber at a rate of at least 2, 3, 4, 5, 10, 15, 20, 25, 30, 35, 40, 45, 50, 55, 60, 65, 70, 75, 80, 85, 90, 95, 100 feet/minute, or higher. The air supply unit and/or exhaust vent or unit may be configured to replace the air inside the chamber at rate of at least 1 air change by hour. In some embodiments, the air inside the chamber is changed at a rate of at least 2, 3, 4, 5, 10, 15, 20, 25, 30, 35, 40, 45, 50, 60, 70, 80, 80, 100, 150, 200, 250, 300, 350, 400, 450, 500, 550, 600 or more air changes per hour.

In some embodiments, the clean chamber provides an air cleanliness that meets ISO 14644-1 Cleanroom Standards, such as ISO 1, ISO 2, ISO 3, ISO 4, ISO 4, ISO 5, ISO 6, ISO 7, ISO 8, and ISO 9. These standards are based on the size and number of airborne particles per cubic meter of air. In other embodiments, the clean chamber provides air cleanliness that meets US Federal Standard 209E Cleanroom Standards, such as Class 1, 10, 100, 1,000, 10,000, 10,000, or 100,000. US Federal Standard 209E Cleanroom Standards are based on the number of particles 0.5 µm or larger per cubic foot of air (e.g. a Class 1,000 cleanroom would indicate 1,000 particles 0.5 µm or smaller in each cubic foot of air). These standards can be met by adjusting the air flow and rate of air replacement inside the clean chamber, which is a function of the volume of air moved by the air supply unit(s) and exhaust unit(s). For example, to meet cleaner air standards, the flow of the air supply units can be increased, or additional air supply units can be fitted in the chamber when the maximum flow is reached. Whether the clean chamber meets the above standards can be confirmed through various testing procedures known in the art, such as those described in the Federal Standard 209 document or IEST-RP-CC-006: TESTING CLEANROOMS, which is available on the Institute of Environmental Sciences and Technology (LEST) website.

The clean chamber may be made of a combination of steel, stainless steel, aluminum, titanium, glass, plastic, or any combination of these materials. In some embodiments, the clean chamber is an enclosure made of a steel, stainless steel, or powder coated steel frame and glass or plastic windows or doors. Further, the edges of the clean chamber may be rounded on the bottom, top, and or sides of the clean chamber. Additionally, the clean chamber may have casters or wheels on the bottom so that it me be easily moved, or feet on the bottom for providing stability on a flat surface such as a benchtop.

Figure 1:
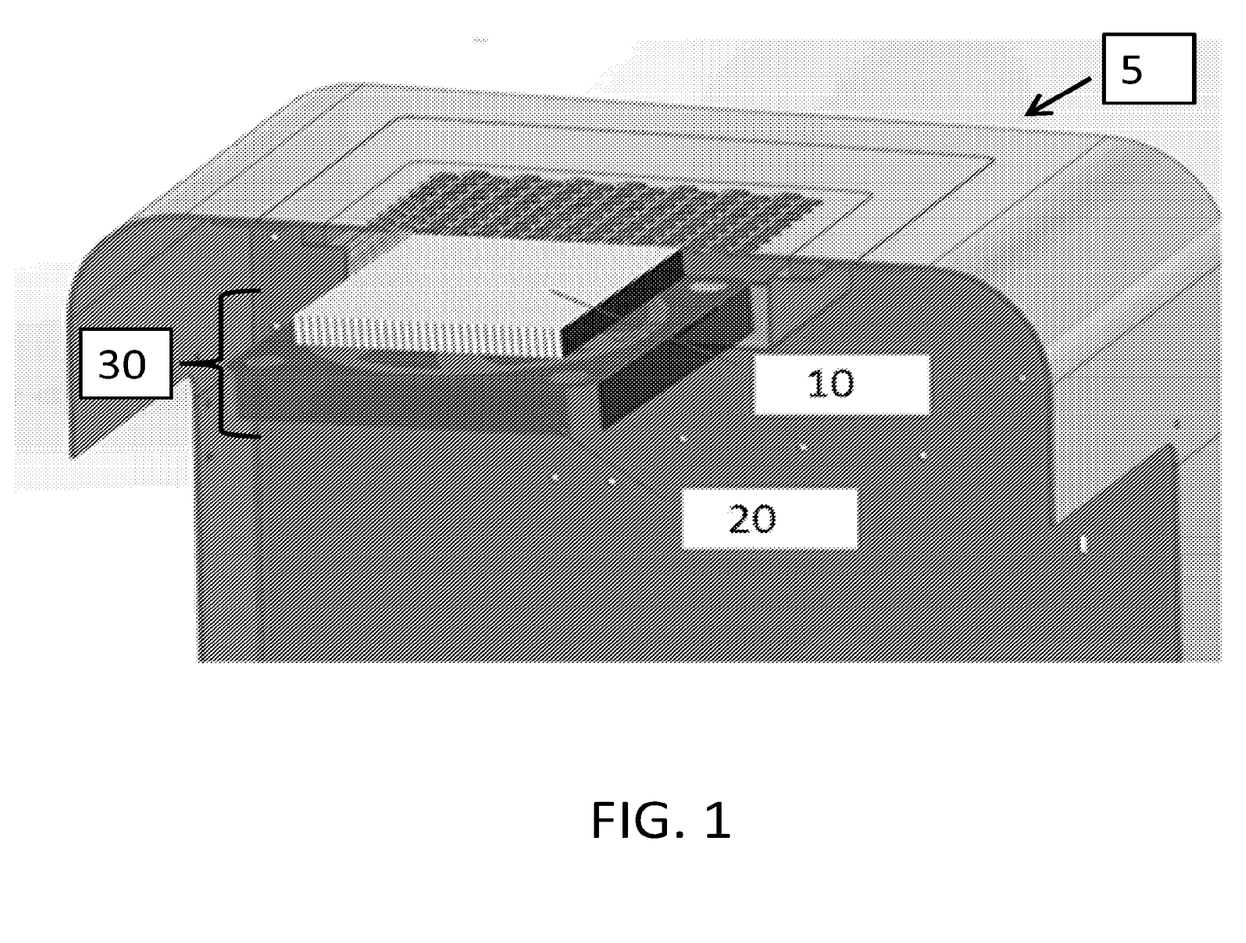
FIG. 1 is a schematic diagram showing a top view of the clean chamber technology according to an embodiment of the invention.
Figure 2:
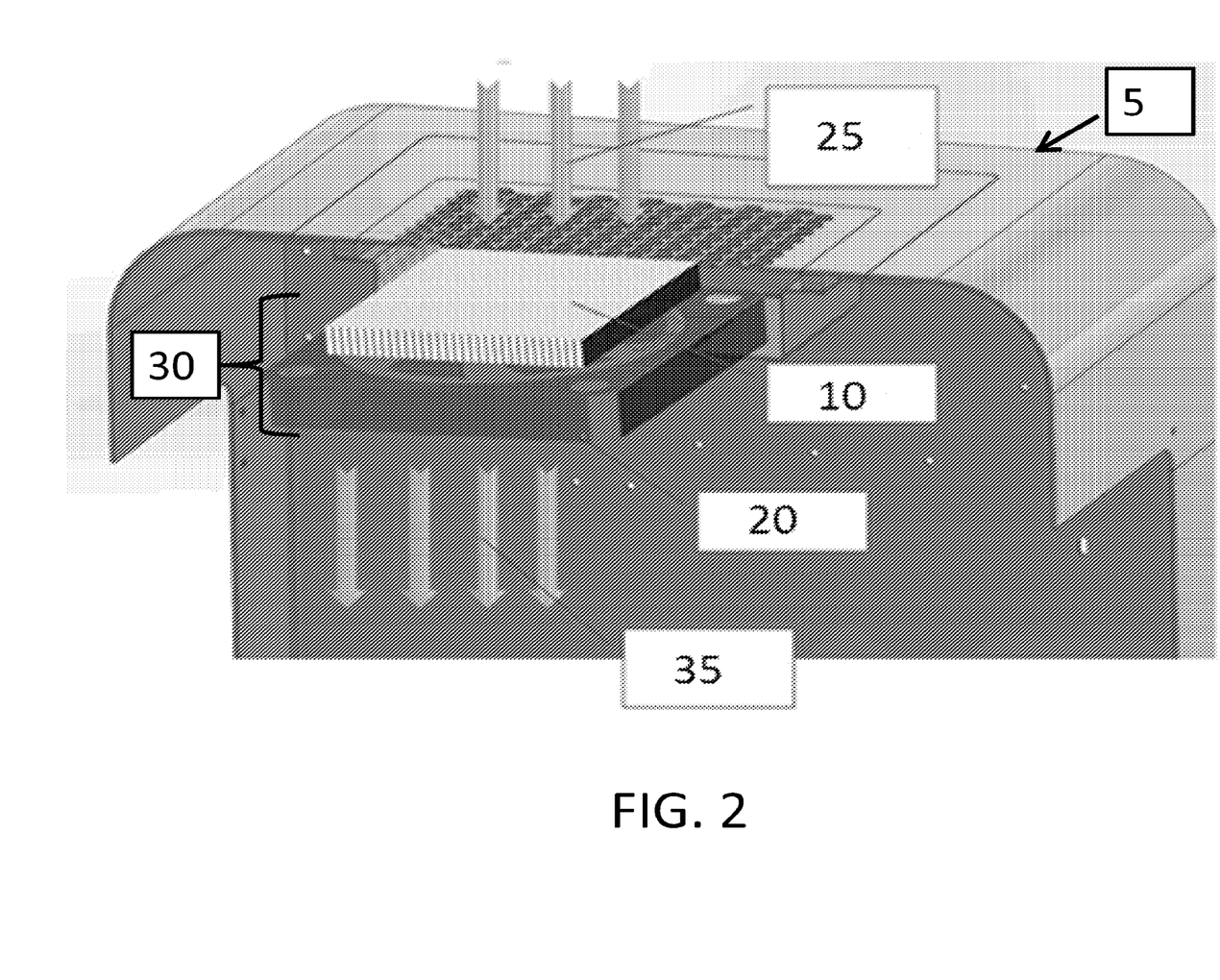
FIG. 2 is a schematic diagram showing a detailed configuration of the high efficiency filter and electrically powered fan according to an embodiment of the invention.

The following figures are intended to illustrate a particular embodiment of the invention. FIG. 1 shows an embodiment of a clean chamber 5 in which an air supply unit 30 is positioned on the top of the clean chamber 5. In this embodiment, the air supply unit 30 includes a HEPA filter 10 and a fan unit 20, where the HEPA filter 10 is positioned immediately before the fan unit 20 at its intake. FIG. 2 shows the embodiment of the clean chamber 5 of FIG. 1, where air 25 from outside the unit enters the air supply unit 30 and passes through it such that the output of air supply unit produces clean and vertical laminar flow 35 through the clean chamber 5 to the 3D printer (not shown). Additional, an exhaust vent (not shown) is positioned on the bottom of the chamber.

Figure 3:
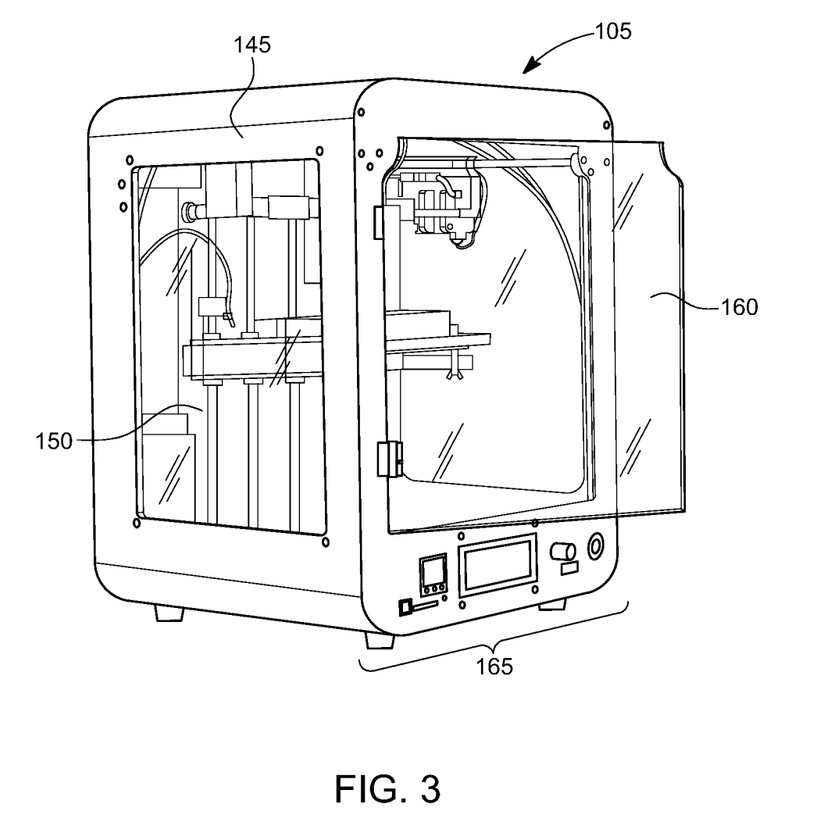
FIG. 3 is a photograph showing a side view of an integrated clean chamber-3D bioprinter according to a particular embodiment of the invention.
Figure 4:
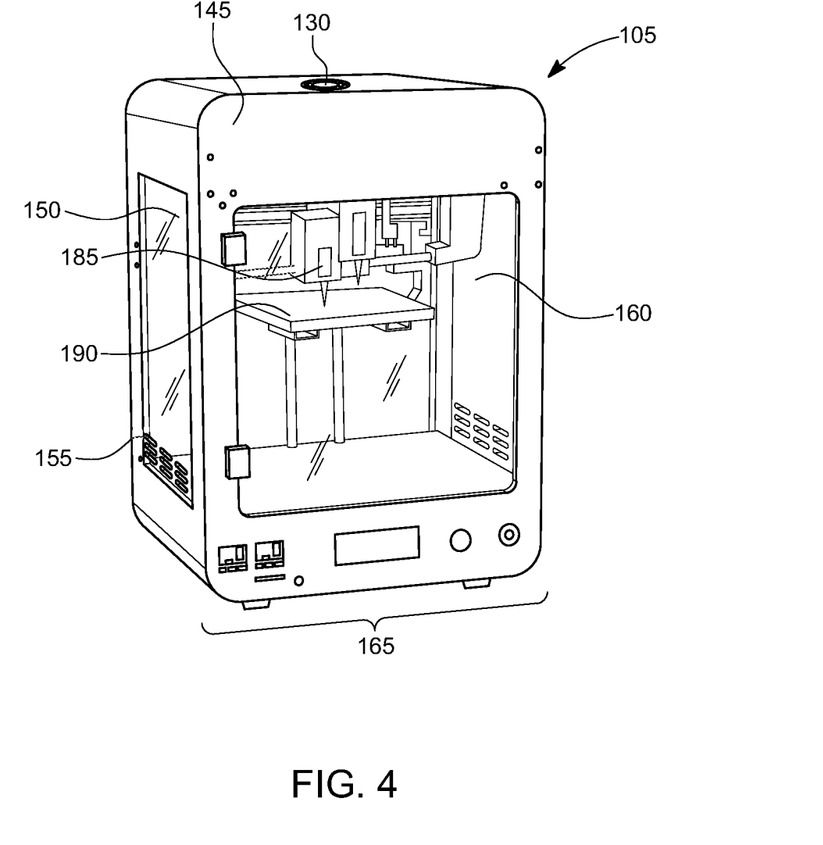
FIG. 4 is a photograph showing a front view of an integrated clean chamber-3D bioprinter according to a particular embodiment of the invention.

FIGS. 3 and 4 show a particular embodiment of a clean chamber housing integrated with a 3D bioprinter. The integrated clean chamber-3D bioprinter 105 has a powder coated steel frame 145 which is designed to be chemically resistant to form a cubicle-shaped housing. The housing further comprises a front door 160 which can have a seal to form an airlock when shut and two windows 150 on either side of the housing for viewing inside. The front door can be made of glass, plexiglass, or plastic to provide a view inside the print bed when the door is shut. On top of the housing is an air supply unit 130, which includes a small fan and HEPA filter. Below the front door of the housing are various displays and controls 165 for interfacing with the 3D bioprinter inside. The displays or controls include displays for pressure sensors and an off/on switch. Inside the housing various components of the 3D bioprinter inside can be seen including a moveable platform or print bed 190 and syringes 185 for extrusion. The moveable print bed can support multiwell plates, petri dishes, and/or glass slides. At the bottom of the window 150 is a vent 155 for discharging air passing through the clean chamber.

Embodiments of the invention provide for additional features of the 3D bioprinter inside the clean chamber which can include the following. The bioprinter can contain a UV curing light with wavelength ranging from 300 nm to 500 nm, as well as a UV light for sterilization of the printing area. The bioprinter can have print heads for printing eukaryotic and prokaryotic cells within, on and without hydrogels. The print heads can dispense materials with dynamic viscosity ranges of 1 to 20,000,000 centiPoise (cP). The print heads can be used to dispense biomaterials, hydrogels, materials prepared from decellularized human and animal tissues and organs, as well as cells in suspension in a defined and non-defined pattern. The print heads are capable of dispensing these biomaterials to create a 3D structure, including those containing eukaryotic and prokaryotic cells. In embodiments, the bioprinter can contain between 1 to 20 print heads, such as 1, 2, 3, 4, 5, 6, 7, 8, 9, 10, 11, 12, 13, 14, 15, 16, 17, 18, 19, or 20 print heads. The print heads can be positioned apart from each other with a distance of between 1 mm to 100 mm. The print heads can dispense material such as bioinks through needles with straight or conical tips and co-axial needles. The bioinks can be mixed with human cells prior to dispensing. Further, embodiments provide a print bed where the material can be dispensed on a removable substrate or directly on top of the print bed itself. The print bed can hold petri dishes, multi well plates, and/or glass slides. The bioprinter dispenses materials using pneumatic pressure, mechanical pressure, heated extrusion, hydraulic extrusion, or pneumatic extrusion, or by way of a jet printer with piezoelectric applicator or jet dispenser with pneumatic applicator. In embodiments, the print heads and print beds are positioned under the high efficiency air filter(s) so that they directly receive filtered air entering the clean chamber. The filtered air and positive pressure created inside the clean chamber allows for sterile printing of cell-laden and cell-free 3D structures.

In alternative embodiments, the housing can accommodate a 3D printer or bioprinter of a variety of other configurations, non-limiting examples of which are described in U.S. Pat. Nos. 7,051,654, 8,241,905, 8,691,274, 9,149,952 as well as U.S. Patent Application Publication No. 20130302872. This invention contemplates that the housing can be configured to house any 3D printer or bioprinter known in the art, as well as future improvements in 3D printer or bioprinter technology. The housing of the clean chamber can be manufactured together with the 3D printer or bioprinter in an integrated fashion, or alternatively, it can be retrofitted to accommodate the 3D printer or bioprinter.

Additional embodiments provide a kit for 3D printing or 3D bioprinting. The kit includes an integrated clean chamber-3D bioprinter, as well as various reagents and consumables for use in the 3D bioprinter such as hydrogels, syringes, binding agents, cells, multiwell plates, petri dishes, replacement filters, and the like.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A laboratory instrument, comprising:
   a clean chamber, comprising:
      a housing comprising a frame;
      an air supply unit and one or more vents disposed within the frame of the housing, wherein the air supply unit comprises a filter and a fan, blower, or air pump, wherein the filter is a HEPA or ULPA filter, and wherein the air supply unit is disposed within the frame at a top of the housing and does not extend past a top surface plane of the housing and wherein the one or more vents do not comprise a filter; and a 3D bioprinter comprising:

a 3D print bed;

one or more fluid sources adapted for 3D printing disposed above the print bed;

wherein the 3D bioprinter is disposed within the housing such that the 3D print bed is disposed between the air supply unit and the one or more vents;

wherein the clean chamber is capable of maintaining positive pressure inside by way of the air supply unit;

wherein the instrument is dimensioned to have a depth of 60 cm or less; and wherein the instrument is suitable for printing living cells.

2. The laboratory instrument of claim 1, wherein the housing further comprises one or more controls or displays for interfacing with the 3D printer.

3. The laboratory instrument of claim 1, wherein the housing further comprises a door adapted for providing access inside the housing.

4. The laboratory instrument of claim 1, wherein the housing further comprises at least one window adapted for viewing inside the housing.

5. The laboratory instrument of claim 1, wherein the one or more vents are disposed at the sides or the bottom of the housing.

6. The laboratory instrument of claim 1, wherein the housing comprises one or more of steel, stainless steel, aluminum, titanium, glass, or plastic.

7. The laboratory instrument of claim 1, wherein the positive pressure is a positive differential pressure in the range of 0.02 inch to 0.2 inch water column.

8. The laboratory instrument of claim 1, wherein the air supply unit and one or more vents are configured to provide vertical laminar flow.

9. The laboratory instrument of claim 8, wherein the vertical laminar flow is disposed above the 3D print bed.

10. The laboratory instrument of claim 1, wherein the instrument is dimensioned to be less than 0.5 $m^3$.

11. The laboratory instrument of claim 1, wherein the instrument is dimensioned to have a footprint that is smaller than the width of a standard laboratory bench.

12. The laboratory instrument of claim 11, wherein the 3D print bed is adapted to support a multiwell plate or a petri dish.

* * * * *

UNITED STATES PATENT AND TRADEMARK OFFICE
CERTIFICATE OF CORRECTION

| | |
|---|---|
| PATENT NO. | : 11,370,171 B2 |
| APPLICATION NO. | : 15/755767 |
| DATED | : June 28, 2022 |
| INVENTOR(S) | : Erik Gatenholm, Ivan Tournier and Paul Gatenholm |

It is certified that error appears in the above-identified patent and that said Letters Patent is hereby corrected as shown below:

On the Title Page

Item (71) please change "Applicant: BICO Groug AB, Gothenburg (SE)" to --Applicant: BICO Group AB, Gothenburg (SE)--.

Signed and Sealed this
Twenty-fifth Day of October, 2022

Katherine Kelly Vidal
*Director of the United States Patent and Trademark Office*